ns Patent [19]

Kamada et al.

[11] 4,147,876
[45] Apr. 3, 1979

[54] EASILY HYDROLYZABLE ESTERS OF 4-(2-CARBOXYETHYL)PHENYL TRANS-4-AMINOMETHYLCYCLOHEXANECARBOXYLATE AND PROCESS OF USE

[75] Inventors: Masahiro Kamada; Masataka Mimura, both of Tokyo, Japan

[73] Assignee: Daiichi Seiyaku Co., Ltd., Tokyo, Japan

[21] Appl. No.: 901,632

[22] Filed: May 1, 1978

[51] Int. Cl.² .................. C07C 101/02; A61K 31/24
[52] U.S. Cl. .................. 560/37; 260/465 D; 424/309; 560/45
[58] Field of Search ............ 560/37; 260/465 D

[56] References Cited
U.S. PATENT DOCUMENTS
3,699,149  10/1972  Yamamura et al. ............ 560/125

OTHER PUBLICATIONS
McOmie, Protective Groups in Organic Chemistry, Plenum Press, N.Y., N.Y., pp. 206–212 (1973).
Okano et al., J. of Med. Chem., vol. 15, No. 3, pp. 247–255 (1972).
Stelakatos et al., J. Chem. Soc. (C), 1191 (1966).

Primary Examiner—James O. Thomas, Jr.
Assistant Examiner—G. T. Breitenstein
Attorney, Agent, or Firm—Oblon, Fisher, Spivak, McClelland & Maier

[57] ABSTRACT

New intermediates represented by the formula:

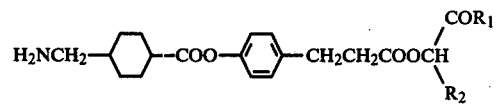

wherein $R_1$ is a lower alkyl group, a substituted lower alkyl group, an aryl group, a lower alkoxy group or an amino group and $R_2$ is a hydrogen atom, a lower alkyl group, an aryl group, a lower acyl group, a lower alkoxycarbonyl group or a cyano group can be converted to 4'-(2-carboxyethyl)phenyl trans-4-aminomethylcyclohexanecarboxylate by selectively hydrolyzing the intermediate.

12 Claims, No Drawings

EASILY HYDROLYZABLE ESTERS OF 4-(2-CARBOXYETHYL)PHENYL TRANS-4-AMINOMETHYLCYCLOHEXANECARBOXYLATE AND PROCESS OF USE

BACKGROUND OF THE INVENTION

1. Field of the Invention

This invention relates to intermediates useful in preparing 4'-(2-carboxyethyl)phenyl trans-4-aminomethylcyclohexanecarboxylate (hereinafter referred to as CEP-ester), a compound which is pharmaceutically useful in an anti-plasmin agent or anti-peptic ulcer agent, and its therapeutically useful acid addition salts. More particularly it relates to novel esters which are easily hydrolyzed to yield CEP-ester, and to processes for producing CEP-ester using these novel esters.

2. Description of the Prior Art

Three processes are known for producing CEP-ester.

(i) The intermediate 4'-(2-benzyloxycarbonylethyl)-phenyl trans-4-N-benzyloxycarbonyl aminomethylcyclohexanecarboxylate hydrochloride or 4'-(2-benzyloxycarbonylethyl)phenyl trans-4-aminomethylcyclohexanecarboxylate hydrochloride is catalytically reduced with hydrogen, whereby the benzyloxycarbonyl protecting groups are removed to yield CEP-ester. The necessary intermediates are obtained by condensing trans-4-N-benzyloxycarbonylaminomethylcyclohexanecarbonyl chloride or trans-4-aminomethylcyclohexanecarbonyl chloride, respectively, with benzyl 4-hydroxyphenylpropionate. This process is disclosed in Japanese Published Examined Patent Applications 19950/71 and 48978/77.

(ii) The intermediate 4'-(2-tert-butoxycarbonylethyl)-phenyl trans-4-aminomethylcyclohexanecarboxylate hydrochloride is treated with hydrogen halide-acetic acid to remove the carbonyl protecting group, i.e., the tert-butyl group, and thus yield CEP-ester. The intermediate is prepared by condensing trans-4-aminomethylcyclohexanecarbonyl chloride with tert-butyl 4-hydroxyphenylpropionate. This process is disclosed in Japanese Published Unexamined Patent Application No. 78143/73.

The use of special and very specific protecting groups in the two processes described above is essential for the following reasons. In the condensation reaction used to prepare the intermediates used in the processes the carboxyl group of the 4-hydroxyphenylpropionic acid must be protected to prevent it from reacting with the acid halide. Therefore, after the condensation reaction, the protective group which remains attached to the terminal carboxyl group must be selectively removed to obtain the target CEP-ester. The carboxyl group cannot be protected by forming a conventional ester because the phenyl ester linkage in CEP-ester is much more easily hydrolyzed than ester linkages generally and hence will be preferentially hydrolyzed with resulting cleavage of the molecule and poor yield of CEP-ester. Hence, the protective group must be a special group which is easily removed by catalytic hydrogenation or special conditions of hydrolysis.

This problem is well illustrated by the third conventional method of preparing CEP-ester which does not use a special protective group and accordingly, suffers from poor yield.

(iii) The intermediate 4'-(2-alkoxycarbonylethyl)phenyl trans-4-aminomethylcyclohexanecarboxylate or its acid addition salt is hydrolyzed in the presence of an acid catalyst to give CEP-ester. The intermediate is prepared by reacting an alkyl 4-hydroxyphenylpropionate with trans-4-aminomethylcyclohexanecarbonyl chloride. This process is disclosed in Japanese Published Unexamined Patent Application No. 17447/77.

Method (iii) is the simplest of the conventional processes for producing CEP-ester. However, since the yield is less than 35% it is not industrially advantageous. The low yield is due to the fact that the molecule contains two types of ester linkages, the phenyl ester linkage and the alkyl ester linkage. In hydrolysis the alkyl ester linkage is only slightly less stable than the phenyl ester linkage. Hence the alkyl ester linkage cannot be hydrolyzed exclusively and some of the phenyl ester linkages are hydrolyzed with resultant lowering of the yield.

Hence, a need has continued to exist for a method of preparing CEP-ester in good yield, without using special protecting groups for the terminal carboxyl group.

SUMMARY OF THE INVENTION

Accordingly, it is an object of this invention to provide novel intermediates for use in synthesizing CEP-ester.

A further object is to provide esters which can be easily hydrolyzed to yield CEP-ester.

A further object is to provide easily prepared esters devoid of special protecting groups which can be easily hydrolyzed to yield CEP-ester.

A further object of the invention is to provide esters which can be easily hydrolyzed to give CEP-ester in good yield.

A further object is to provide a method for synthesizing CEP-ester in good yield.

Further objects of the invention will become apparent from the following description of the invention.

As a result of intensive investigation of processes for producing CEP-ester, the inventors have achieved the objects of their invention.

According to the invention CEP-ester, represented by formula (III) can easily be obtained by hydrolyzing the novel compound having formula (II), using conventional techniques of hydrolysis. The novel compound (II) can be prepared by condensing the novel compound (I) with a trans-4-aminomethylcyclohexanecarbonyl halide.

Thus, the intermediates of this invention and the process of using them can be schematically represented as follows:

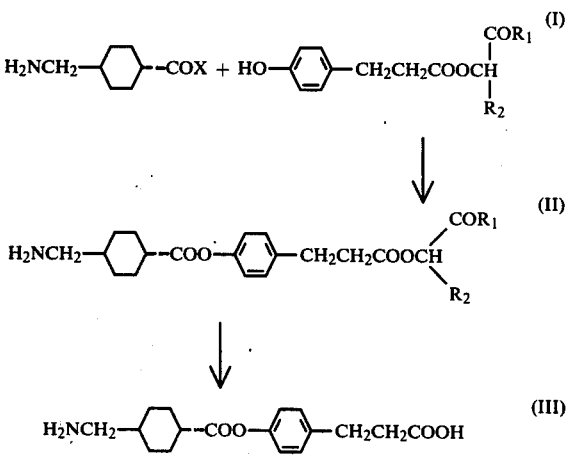

wherein X represents a halogen atom, $R_1$ represents a lower alkyl group, a substituted lower alkyl group, an aryl group, a lower alkoxy group or an amino group, and $R_2$ represents a hydrogen atom, a lower alkyl group, an aryl group, a lower acyl group, a lower alkoxycarbonyl group or a cyano group.

The step of hydrolyzing the intermediate (II) to CEP-ester (III) may be carried out in water or aqueous organic solvent at temperatures between 0° and 100° C., optionally in the presence of a base.

The step of condensing the starting compound (I) with trans-4-aminomethylcyclohexanecarbonyl chloride may be carried out in any inert solvent for the reagents at a temperature in the range of 30° C. to 110° C.

DETAILED DESCRIPTION OF THE PREFERRED EMBODIMENTS

The novel intermediate (II) contains two ester linkages which have different stability with respect to hydrolytic cleavage. In general, the acetonyl ester linkage is more easily hydrolyzed than the phenyl ester linkage. Therefore, when the intermediate (II) is hydrolyzed under weakly acidic or weakly alkaline conditions at ordinary temperatures, the acetonyl ester linkage is hydrolyzed while the phenyl ester linkage remains unhydrolyzed. Hence, CEP-ester is obtained directly from the intermediate (II) under mild conditions and in good yield. Thus, the intermediates (II) are superior to previously known intermediates used in the production of CEP-ester and accordingly are very useful and important compounds in the industrial production of CEP-ester.

In the formula for the intermediate (II) $R_1$ may be a lower alkyl group, such as methyl, ethyl, 1-propyl, 2-propyl, 1-butyl, 2-butyl, tert-butyl, 1-pentyl, or 1 hexyl; a substituted lower alkyl group, especially a haloalkyl group, such as chloromethyl, bromomethyl, 1-chloroethyl, 2-chloroethyl, 3-chloropropyl, 4-chlorobutyl; an aryl group such as a phenyl group; a lower alkoxy group, such as methoxy, ethoxy, 1-propoxy, 2-propoxy, 1-butoxy, 2-butoxy, tert-butoxy, 1-pentoxy, 1-hexoxy; or an amino group. $R_2$ may be a hydrogen atom, a lower alkyl group, such as methyl, ethyl, 1-propyl, 2-propyl, 1-butyl, 2-butyl, 1-pentyl, 1-hexyl; an aryl group such as a phenyl group; a lower acyl group such as acetyl, propionyl, butyryl, pentanoyl, hexanoyl; a lower alkoxycarbonyl group such as methoxycarbonyl, ethoxycarbonyl, 1-propoxycarbonyl, 2-propoxycarbonyl, 1-butoxycarbonyl, 2-butoxycarbonyl, tert-butoxycarbonyl, 1-pentoxycarbonyl, 1-hexoxycarbonyl; or a cyano group.

The term "lower" as applied to the alkyl, substituted alkyl acyl, and alkoxycarbonyl groups signifies, as is well known to those skilled in the art, a group containing a relatively small number of carbon atoms, that is, a group small enough so that its size or bulk does not interfere with the function of the molecule or with the reactions in which it is involved. While no absolute limit may be set on the number of carbons such a group may contain, the limit will be recognizable by one skilled in the art in a given instance. The number of carbon atoms will generally range from one to about seven.

The substituted lower alkyl groups useful as $R_1$ may contain any substituent which is relatively inert, that is, which is not chemically incompatible with the other functional groups in the molecule and does not, by its chemical reactivity, interfere with the reactions which the molecule undergoes in the processes involved in this invention. The selection of proper substituents will be evident to one skilled in the art from the above disclosure. A typical substituent used in the substituted lower alkyl groups is halogen, e.g., chlorine.

The acid used to form the acid addition salts of this invention may be any acid which does not itself interfere with the function of the particular compound or the reactions which it must undergo. The choice of such acids is conventional and within the competence of the skilled practitioner. Typical acids include hydrohalic acids, sulfuric acid, sulfonic acids and the like.

The novel intermediates (II) may be prepared by reacting a compound of the formula (I) with a trans-4-aminocyclohexanecarbonyl halide, or an acid addition salt thereof, e.g., with trans-4-aminocyclohexanecarbonyl chloride. The reaction is carried out in an inert solvent, that is, one which does not itself react with the reagents and does not otherwise inhibit the reaction. Suitable inert solvents include halogenated hydrocarbons such as dichloroethane, trichloroethane, chloroform; hydrocarbons such as benzene, toluene; ethers such as dioxan, and the like. The reaction may be conveniently carried out at a temperature in the range of 30° to 110° C., preferably 50° to 80° C. After the reaction the desired intermediate compound (II) can be separated from the reaction mixture by conventional techniques, as illustrated in the examples.

The starting material for preparing the novel intermediate of formula (II) is itself a novel compound which is represented by formula (I) and may be named as an alkyl ester of 3-(4-hydroxyphenyl)propionic acid. In formula (I) the radicals $R_1$ and $R_2$ have the same significance as in the compound of formula (II) described above.

The novel starting materials of formula (I) can be made by reacting 3-(4-hydroxyphenyl)propionic acid with a compound of formula (IV).

(IV)

wherein X represents a halogen atom and $R_1$ and $R_2$ are as defined above.

The reaction may be carried out according to conventional procedures by reacting the two reagents in an inert solvent in the presence of a base, at temperatures from 0° C. to 120° C., preferably 80° C. to 90° C. A detailed example of typical conditions for preparing these compounds is given in Example I.

The intermediate of formula (II) is especially useful in the preparation of CEP-ester as pointed out above. The hydrolysis may be conducted by any known hydrolysis procedure. However, it will be understood by the skilled practitioner that both ester linkages in the compound of formula (II) are rather easily hydrolyzed. Hence, the hydrolysis conditions will generally be mild, and the conditions will be adjusted so that the more labile terminal ester linkage is largely hydrolyzed, while the central ester linkage remains for the most part unhydrolyzed. The hydrolysis may be carried out in water or aqueous organic solvents. For example, aqueous solvent of dioxan or acetone, or aqueous alcoholic solvents may also be used. A preferred solvent is water. The hydrolysis may be carried out by suspending the compound of formula (II) in water in the presence or absence of a base. The reaction is usually carried out at a pH in the range 5 to 12. Suitable bases which may be used are hydroxides of alkali or alkaline earth metals such as sodium hydroxide, potassium hydroxide, barium hydroxide, and the like; alkali or alkaline earth metal salts of weak acids such as sodium carbonate, sodium bicarbonate, potassium carbonate, potassium bicarbonate, sodium acetate, and the like; or organic bases such as pyridine, triethylamine, trimethylamine, diethylamine, dimethylamine, monoethylamine, monomethylamine, or a salt thereof with a weak acid. The amount of base to be used is not particularly limited. As pointed out above, the hydrolysis is carried out at a pH of 5 to 12, and an appropriate amount of base is used to attain the desired pH. When the acid addition salt of the compound of formula (II) is to be hydrolyzed, an equimolar or slightly greater amount of base is sufficient to produce the reaction.

The temperature of the hydrolysis reaction depends on the type of group used as the protective group for the terminal carboxyl group, the type and concentration of the base used, and the pH. The skilled practitioner will have no difficulty determining the optimum reaction conditions. The reaction may be carried out at a temperature between 0° and 100° C., preferably in the range of 20° to 70° C.

Having generally described the invention, a more complete understanding can be obtained by reference to certain specific examples, which are included for purposes of illustration only and are not intended to be limiting unless otherwise specified.

EXAMPLE 1

This example describes the preparation of the novel starting materials of formula (I) used in synthesizing the intermediates of formula (II).

After 49.9 g of 4-hydroxyphenylpropionic acid was dissolved in 160 ml of dimethylformamide, 21.8 g of potassium carbonate was added to the solution at room temperature. Then 29.1 g of monochloroacetone was added dropwise to the solution at 60° C. and the reaction with 4-hydroxyphenylpropionic acid was carried out at 80°-90° C. for 1 hour. After the reaction, dimethylformamide was distilled off from the reaction solution to give a residue. After the residue was dissolved in dichloroethane, the solution was washed with water. The layer of dichloroethane was removed and the solvent was distilled off to give 64.7 g (yield 97%) of acetonyl 4-hydroxyphenylpropionate. After recrystallization from isopropylether, the product was a colorless crystalline material having a melting point of 64.5° C.

Elemental analysis: Calcd. for $C_{12}H_{14}O_4$ C 64.85%, H 6.35%. Found C 64.99%, H 6.39%.

In the same manner, other starting materials (I) were prepared. Their melting points and elemental analyses are shown in Table I.

Table I

Melting points and elemental analyses of starting materials (I):

$$HO-\text{C}_6\text{H}_4-CH_2CH_2COOCH(R_2)(COR_1)$$

| $R_1$ | $R_2$ | Melting point °C. | C | H | N | Cl |
|---|---|---|---|---|---|---|
| $CH_3$ | $CH_3$ | oil | 66.09 / 65.81 | 6.82 / 6.74 | — | — |
| $CH_3$ | $COCH_3$ | oil | 63.63 | 6.10 | — | — |

Table I-continued

Melting points and elemental analyses of starting materials (I):

| $R_1$ | $R_2$ | Melting point °C. | C | H | N | Cl |
|---|---|---|---|---|---|---|
| $CH_3$ | $COOC_2H_5$ | oil | 63.41 / 61.22 / 61.15 | 6.03 / 6.16 / 6.25 | — | — |
| $CH_2Cl$ | H | 86.5 | 56.15 / 56.43 | 5.10 / 5.08 | — | 13.81 / 13.80 |
| $NH_2$ | H | 149.5 | 59.19 / 59.39 | 5.87 / 5.99 | 6.27 / 6.30 | — |
| $C_6H_5$ | H | 78.5 | 71.82 / 71.56 | 5.67 / 5.65 | — | — |
| $OCH_3$ | H | oil | 60.50 / 61.00 | 5.92 / 6.20 | — | — |
| $OC_2H_5$ | $COOC_2H_5$ | oil | 59.25 / 58.98 | 6.22 / 6.25 | — | — |

EXAMPLE 2

63.3 g of acetonyl 4-hydroxyphenylpropionate was reacted with 60.4 g of trans-4-aminomethylcyclohexanecarboxylic acid chloride hydrochloride in 260 ml of 1,2-dichloroethane at 60°-70° C. for 2.5 hours with stirring. After the reaction, a crystalline precipitate was removed by filtration and dried to give 105.5 g (yield: 93.1%) of 4'-(2-acetonyloxycarbonylethyl)-phenyl trans-4-aminomethylcyclohexanecarboxylate hydrochloride. This product was recrystallized from aqueous isopropyl alcohol to give a colorless crystalline material having a melting point of 199° C. (decomp.).

Elemental analysis: Calcd. for $C_{20}H_{28}NO_5Cl$ C=60.37 H=7.09 N=3.52 Cl=8.91%. Found C=60.45 H-7.02 N=3.61 Cl=9.04%.

4.97 g of 4'-(2-acetonyloxycarbonylethyl)phenyl trans-4-aminomethylcyclohexanecarboxylate hydrochloride obtained as above and an aqueous solution containing 2.10 g of sodium bicarbonate were mixed and allowed to react at 40° C. for 40 hours with stirring. After the reaction, precipitated crystals were filtered off and dried to give 3.56 g (yield: 93.4%) of 4'-(2-carboxyethyl)phenyl trans-4-aminomethylcyclohexanecarboxylate (CEP-ester). This product was identified by nuclear magnetic resonance (NMR) spectra and infrared (IR) spectra. Then, the product was treated with diluted hydrochloric acid to give 3.84 g (yield: 89.9%) of the corresponding hydrochloric acid-addition salt having a melting point of 235° C. (decomp.).

EXAMPLE 3

The hydrochloric acid-addition salt of 4'-(2-acetonyloxycarbonylethyl)phenyl trans-4-aminomethylcyclohexanecarboxylate obtained by the procedure of the first half of Example 2 was dissolved in water and neutralized with a dilute acqueous solution of sodium bicarbonate at room temperature to give a crystalline material. The crystalline material was removed by filtration and recrystallized from aqueous methanol to give the free form of 4'-(2-acetonyloxycarbonylethyl)-phenyl trans-4-aminomethylcyclohexanecarboxylate having a melting point of 144° C. (decomp.).

Elemental analysis: Calcd. for $C_{20}H_{27}NO_5$ C=66.46 H=7.53 N=3.88%. Found C=66.34 H=7.34 N=3.98%.

4.52 g of 4'-(2-acetonyloxycarbonylethyl)phenyl trans-4-aminomethylcyclohexanecarboxylate obtained as above was suspended in 60 ml of water and then hydrolyzed at 40° C. for 40 hours with stirring. After the reaction, the solution was treated by the procedure described in the latter half of Example 1 to give 3.25 g (yield: 85.1%) of CEP-ester. The obtained product was identified by NMR and IR-spectra.

EXAMPLE 4

8:50 g of α-methylacetonyl 4-hydroxyphenylpropionate was reacted with 6.37 g of trans-4-aminomethylcyclohexanecarbonyl chloride hydrochloride in 50 ml of 1,2-dichloroethane at 65°–70° C. for 3.5 hours with stirring. After the reaction, the solvent was distilled off the reaction solution and the residue was recrystallized from isopropyl alcohol to give 9.74 g (yield: 78.4%) of 4'-[2-(α-methylacetonyloxycarbonyl)ethyl]phenyl trans-4-aminomethylcyclohexanecarboxylae hydrochloride having a melting point of 187° C. (decomp.).

Elemental analysis: Calcd. for $C_{21}H_{30}NO_5Cl$ C=61.23 H=7.43 N=3.40 Cl=8.61% Found C=61.20 H=7.29 N=3.46 Cl=8.46%

5.15 g of 4'-[2-(α-methylacetonyloxycarbonyl)ethyl]phenyl trans-4-aminomethylcyclohexanecarboxylate hydrochloride obtained as above was added to 100 ml of 5% sodium bicarbonate aqueous solution and hydrolyzed at 40° C. for 24 hours with stirring. The reaction solution was treated by the procedure used in the latter half of Example 2 to give 3.17 g (yield: 83.0%) of CEP-ester. This product was identified by NMR and IR-spectra.

EXAMPLE 5

15.86 g of α-acetylacetonyl 4-hydroxyphenylpropionate was reacted with 10.60 g of trans-4-aminomethylcyclohexanecarbonyl chloride hydrochloride in 50 ml of 1,2-dichloroethane at 65°–70° C. for 3 hours with stirring. After reaction, the solvent was distilled off and the obtained residue was dissolved in ether. A crystalline precipitate formed which was removed by filtration and dried to give 21.0 g (yield: 95.5%) of 4'-[2-(α-acetylacetonyloxycarbonyl)ethyl]phenyl trans-4-aminomethylcyclohexanecarboxylate hydrochloride. This product was recrystallized from isopropyl alcohol to give a pale-yellow crystalline material having a melting point of 144° C. (decomp.).

Elemental analysis: Calcd. for $C_{22}H_{30}NO_6Cl$ C=60.06 H=6.87 N=3.18 Cl=8.06%. Found C=59.95 H=6.80 N=3.46 Cl=8.09%.

5.50 g of 4-[2-(α-acetylacetonyloxycarbonyl)ethyl]phenyl trans-4-aminomethylcyclohexanecarboxylate hydrochloride obtained as above was added to 100 ml of 5% sodium bicarbonate aqueous solution. Then the hydrolysis was carried out at 40° C. for 29 hours with stirring. The reaction solution was treated by the procedure used in the latter half of Example 2 to give 2.79 g (yield: 73.0%) of CEP-ester. This product was identified by NMR and IR-spectra.

EXAMPLE 6

17.70 g of α-ethoxycarbonylacetonyl 4-hydroxyphenylpropionate was reacted with 10.60 g of trans-4-aminomethylcyclohexanecarbonylchloride hydrochloride in 50 ml of ethylene dichloride at 65°–70° C. for 3 hours with stirring. After reaction, the solvent was distilled off and the obtained residue was dissolved in ether. A crystalline precipitate formed which was removed by filtration. The obtained precipitate was recrystallized from isopropyl alcohol-n-hexane to give 17.05 g (yield: 72.6%) of 4'[2-(α-ethoxycarbonylacetonyloxycarbonyl)ethyl]phenyl trans-4-aminomethylcyclohexanecarboxylate hydrochloride having a melting point of 140° C. (decomp.).

Elemental analysis: Calcd. for $C_{23}H_{32}NO_7Cl$ C=58.78 H=6.86 N=2.98 Cl=7.54%. Found C=58.62 H=6.88 N=2.88 Cl=7.44%.

5.87 g of 4'-[2-(α-ethoxycarbonylacetonyloxycarbonyl)ethyl]phenyl trans-4-aminomethylcyclohexanecarboxylate hydrochloride was dissolved in 100 ml of 5% sodium bicarbonate aqueous solution. Then, the solution was treated by the procedure used in the latter half of the process of Example 4 to give 2.74 g (yield: 71.9%) of CEP-ester. This product was identified by NMR and IR-spectra.

EXAMPLE 7

1.80 g of γ-chloroacetonyl 4-hydroxyphenylpropionate was made to react with 1.48 g of trans-4-aminomethylcyclohexanecarbonyl chloride hydrochloride in 10 ml of ethylene dichloride at 65°–70° C. for 3 hours with stirring. After the reaction, the crystalline reaction product was filtered off and dried to give 2.62 g (yield: 86.8%) of 4'-[2-(γ-chloroacetonyloxycarbonyl)ethyl]phenyl trans-4-aminomethylcyclohexanecarboxylate hydrochloride. On recrystallization from aqueous isopropyl alcohol, the obtained product was a colorless crystalline material and had a melting point of 200° C. (decomp.).

Elemental analysis: Calcd. for $C_{20}H_{27}NO_5Cl_2$ C=55.56 H=6.29 N=3.24 Cl=16.40%. Found C=55.63 H=6.20 N=3.44 Cl=16.17%.

5.40 f of 4'-[2-(γ-chloroacetonyloxycarbonyl)ethyl]phenyl trans-4-aminomethylcyclohexanecarboxylate hydrochloride was dissolved in 100 ml of 5% sodium bicarbonate. Then the solution was treated by the procedure used in the latter half of the process of Example 4 to give 1.98 g (yield: 52.0%) of CEP-ester. This product was identified by NMR and IR-spectra.

EXAMPLE 8

12.0 g of phenacyl 4-hydroxyphenylpropionate was reacted with 8.49 g of trans-4-aminomethylcyclohexanecarbonyl chloride hydrochloride in 50 ml of ethylene dichloride. The reaction solution was treated in the same manner as described in the first half of the process of Example 2 to give 16.09 g (yield: 87.4%) of 4'-(2-phenyacyloxycarbonylethyl)phenyl trans-4-aminomethylcyclohexanecarboxylate hydrochloride. On recrystallization from water, the obtained product was a colorless crystalline material and had a melting point of 205=C. (decomp.).

Elemental analysis: Calcd. for $C_{25}H_{30}NO_5Cl$ C=65.28 H=6.57 N=3.05 Cl=7.71%. Found C=65.22 H=6.49 N=3.00 Cl=7.43%.

5.75 g of 4'-(2-phenacyloxycarbonylethyl)phenyl trans-4-aminomethylcyclohexanecarboxylate hydrochloride obtained as above and 5.3 g of sodium bicarbonate were dissolved in 100 ml of 50% aqueous-acetone and the solution was kept at 50° C. for 45 hours with stirring. After the reaction, the reaction solution was treated by the procedure used in the latter half of the process of Example 2 to give 1.83 g (yield: 47.9) of CEP-ester. This product was identified by NMR and IR-spectra.

EXAMPLE 9

2.23 g of carbamylmethyl 4-hydroxyphenylpropionare was reacted with 2.11 g of trans-4-aminomethylcyclohexanecarbonyl chloride hydrochloride in 30 ml of dioxane at 75°–80° C. for 1.5 hours with stirring. After the reaction, a crystalline precipitate was removed by filtration and dried to give 2.80 g (yield: 70.5%) of 4'-(2-carbamylmethoxycarbonylethyl)phenyl trans-4-aminomethylcyclohexanecarboxylate hydrochloride. This substance was recrystallized from methanol to give a colorless crystalline material having a melting point 242° C. (decomp.).

Elemental analysis: Calcd. for $C_{19}H_{27}N_2O_5Cl$ C=57.21 H=6.82 N=7.02 Cl=8.89%. Found C=57.02 L H=6.74 N=7.01 Cl=9.16%.

4.99 g of 4'-(2-carbamymethyloxycarbonylethyl)phenyl trans-4-aminomethylcyclohexanecarboxylate hydrochloride obtained as above was dissolved in 50 ml of 5% sodium bicarbonate aqueous solution and hydrolyzed at 50° C. for 10 hours with stirring. The reaction solution was treated by the procedure used in the latter half of the process of Example 2 to give 1.32 g (yield: 34.6%) of CEP-ester. This product was identified by NMR and IR-spectra.

EXAMPLE 10

4.76 g of methoxycarbonylmethyl 4-hydroxyphenylpropionate was reacted with 4.23 g of trans-4-aminomethylcyclohexanecarbonyl chloride hydrochloride in 30 ml of 1,2-dichloroethane under the same reaction conditions as in the first half of Example 4 to give 7.30 g (yield: 88.5%) of 4'-(2-methoxycarbonylmethyloxycarbonylethyl)phenyl trans-4-aminomethylcyclohexanecarboxylate hydrochloride. This product was recrystallized from ethanol to give a colorless crystalline material having a melting point of 198° C. (decomp.).

Elemental analysis: Calcd. for $C_{20}H_{28}NO_6Cl$ C=58.04 H=6.82 N=3.38 Cl=8.57%. Found C=58.12 H=6.87 N=3.33 Cl=8.35%.

EXAMPLE 11

10.8 g of diethoxycarbonylmethyl 4-hydroxyphenylpropionate was reacted with 6.36 g of trans-4-aminomethylcyclohexanecarbonyl chloride hydrochloride in 30 ml of 1,2-dichloroethane under the same conditions as in the first half of Example 5 to give 12.7 g (yield 84.7%) of 4'-(2-diethoxycarbonylmethyloxycarbonylethyl)phenyl trans-4-aminomethylcyclohexanecarboxylate hydrochloride. On crystallization from isopropyl alcohol, the produce was a colorless crystalline material and had a melting point of 131° C. (decomp.).

Elemental analysis: Calcd. for $C_{24}H_{34}NO_8Cl$ C=57.65 H=6.85 N=2.80 Cl=7.09%. Found C=57.35 H=6.61 N=2.77 Cl=6.98%.

EXAMPLE 12

4.97 g of 4'-(2-acetonyloxycarbonylethyl)phenyl trans-4-aminomethylcyclohexanecarboxylate hydrochloride obtained by the procedure of the first half of Example 1 was dissolved in 100 ml of water. To the solution, 6.0 ml of 10% sodium hydroxide aqueous solution was added. Then the solution was stirred at 40° C. for 3 hours to effect the hydrolysis. The reaction solution was treated by the procedure used in the latter half of Example 2 to give 2.32 g (yield: 60.9%) of CEP-ester. This product was identified by NMR and IR-spectra.

EXAMPLE 13

4.97 g of 4'-(2-acetonyloxycarbonylethyl)phenyl trans-4-aminomethylcyclohexanecarboxylate hydrochloride obtained by the procedure of the first half of Example 1 was dissolved in 50 ml of water. To the solution, 35 ml of 2% sodium carbonate aqueous solution was added. Then the solution was stirred at room temperature for 43 hours for the purpose of carrying out the hydrolysis reaction. The reaction solution was then treated by the procedure used in the latter half of Example 2 to give 3.14 g (yield: 82.4%) of CEP-ester. This product was identified by NMR and IR-spectra.

EXAMPLE 14

4.97 g of 4'-(2-acetonyloxycarbonylethyl)phenyl trans-4-aminomethylcyclohexanecarboxylate hydrochloride obtained by the procedure of the first half of Example 2 was dissolved in 50 ml of water. To the solution, 1.34 g of triethylamine was added. Then the solution was stirred at 40° C. for 17 hours for the purpose of carrying out the hydrolysis. After the hydrolysis reaction was complete, the reaction solution was treated by the procedure used in the latter half of Example 2 to give 2.89 g (yield: 75.9%) of CEP-ester. This product was identified by NMR and IR-spectra.

Having now fully described the invention, it will be apparent to one of ordinary skill in the art that many changes and modifications can be made thereto without departing from the spirit or scope of the invention as set forth herein.

What is claimed as new and sought to be covered by letters patent is:

1. A compound having the formula

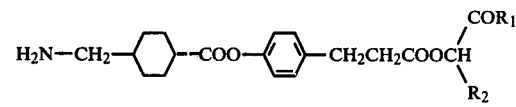

wherein $R_1$ is a member selected from the group consisting of lower alkyl, substituted lower alkyl, aryl, lower alkoxy, and amino, and $R_2$ is a member selected from the group consisting of hydrogen, lower alkyl, aryl, lower acyl, lower alkoxycarbonyl, and cyano, and acid addition salts thereof.

2. The compound of claim 1 which is 4'-(2-acetonyloxycarbonylethyl)phenyl trans-4-aminomethylcyclohexanecarboxylate and its acid-addition salts.

3. The compound of claim 1 which is 4'-[2-(α-methylacetonyloxycarbonyl)ethyl]phenyl trans-4-aminomethylcyclohexanecarboxylate and its acid-addition salts.

4. The compound of claim 1 which is 4'-[2-(α-acetylacetonyloxycarbonyl)ethyl]phenyl trans-4-aminomethylcyclohexanecarboxylate and its acid-addition salts.

5. The compound of claim 1 which is 4'-[2-(α-ethoxycarbonylacetonylcarbonyl)ethyl]phenyl trans-4-aminomethylcyclohexanecarboxylate and its acid-addition salts.

6. The compound of claim 1 which is 4'-[2-(γ-chloroacetonyloxycarbonyl)ethyl]phenyl trans-4-aminomethylcyclohexanecarboxylate and its acid-addition salts.

7. The compound of claim 1 which is 4'-(2-phenacyloxycarbonylethyl)phenyl trans-4-aminomethylcyclohexanecarboxylate and its acid-addition salts.

8. The compound of claim 1 which is 4'-(2-carbamylmethoxycarbonylethyl)phenyl trans-4-aminomethylcyclohexanecarboxylate and its acid-addition salts.

9. The compound of claim 1 which is 4'-(2-methoxycarbonylmethyloxycarbonylethyl)phenyl trans-4-aminomethylcyclohexanecarboxylate and its acid-addition salts.

10. The compound of claim 1 which is 4'-(2-diethoxycarbonylmethyloxycarbonylethyl)phenyl trans-4-aminomethylcyclohexanecarboxylate and its acid-addition salts.

11. A process for producing 4'-(2-carboxyethyl)phenyl trans-4aminomethylcyclohexanecarboxylate or its therapeutically useful acid-addition salts comprising hydrolyzing a compound represented by the formula:

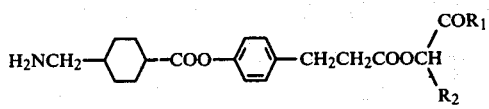

wherein $R_1$ is a member selected from the group consisting of lower alkyl, substituted lower alkyl, aryl, lower alkoxy an amino and $R_2$ is a member selected from the group consisting of hydrogen, lower alkyl, aryl, lower acyl, lower alkoxycarbonyl and cyano, or an acid-addition salt thereof, in water or an aqueous organic solvent, at pH 5-12, and at a temperature of from 0° to 100° C.

12. A process for producing 4'-(2-carboxyethyl)phenyl trans-4-aminomethylcyclohexanecarboxylate or its therapeutically useful acid addition salts which comprises the steps of reacting a trans-4-aminomethylcyclohexanecarbonyl halide with a compound of the formula:

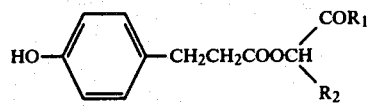

wherein $R_1$ is a member selected from the group consisting of lower alkyl, substituted lower alkyl, aryl, lower alkoxy and amino and $R_2$ is a member selected from the group consisting of hydrogen, lower alkyl, aryl, lower acyl, lower alkoxycarbonyl and cyano, to produce a product compound represented by the formula:

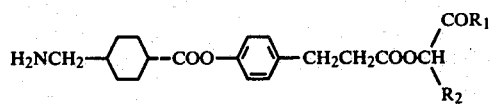

or its acid-addition salt; and subsequently hydrolyzing said product compound in water or an aqueous organic solvent, at pH 5-12, and at a temperature of from 0° to 100° C.

* * * * *